(12) United States Patent
Knowles et al.

(10) Patent No.: US 7,080,562 B2
(45) Date of Patent: Jul. 25, 2006

(54) HIGH-SENSITIVITY PRESSURE CONDUCTION SENSOR FOR LOCALIZED PRESSURES AND STRESSES

(75) Inventors: Gareth Knowles, Williamsport, PA (US); Eli Hughes, State College, PA (US)

(73) Assignee: QorTek, Inc., Williamsport, PA (US)

( * ) Notice: Subject to any disclaimer, the term of this patent is extended or adjusted under 35 U.S.C. 154(b) by 27 days.

(21) Appl. No.: 10/966,892

(22) Filed: Oct. 15, 2004

(65) Prior Publication Data

US 2005/0081640 A1   Apr. 21, 2005

Related U.S. Application Data

(60) Provisional application No. 60/512,335, filed on Oct. 17, 2003.

(51) Int. Cl.
*G01N 3/08* (2006.01)
*H01C 10/10* (2006.01)

(52) U.S. Cl. .............. 73/818; 73/760; 338/47; 338/99; 338/114

(58) Field of Classification Search .......... 73/818, 73/788, 760, 862.391, 862.42, 862.451, 862.471, 73/862.473, 862.474, 862.51, 862.53; 338/47, 338/99, 114
See application file for complete search history.

(56) References Cited

U.S. PATENT DOCUMENTS 3,806,471 A * 4/1974 Mitchell ............... 252/519.31
6,323,751 B1 * 11/2001 Duggal et al. ............ 338/22 R
6,411,191 B1 * 6/2002 Shea et al. ................ 338/22 R
6,646,540 B1 * 11/2003 Lussey ....................... 338/47

FOREIGN PATENT DOCUMENTS

WO   WO 200079546 A1 * 12/2000

* cited by examiner

*Primary Examiner*—Edward Lefkowitz
*Assistant Examiner*—Freddie Kirkland, III
(74) *Attorney, Agent, or Firm*—Michael Crilly, Esq.

(57) ABSTRACT

A high-sensitivity pressure conduction sensor is presented. The present invention includes a pair of locally resilient conductive layers and a locally resilient pressure conduction composite disposed between and contacting both conductive layers. Alternate embodiments include at least three locally resilient conductive layers and at least two locally resilient pressure conduction composites, each having a critical percolation threshold. Each composite is disposed between and contacting two conductive layers in a multi-layer fashion. Other embodiments include a locally resilient pressure conduction composite, a flexible substrate completely surrounding the composite so as to seal it therein, and a pair of electrical leads contacting the composite and terminating outside of the flexible substrate. Pressure conduction composites are composed of a plurality of conductive particles electrically isolated within a non-conductive matrix. Conductive particles are loaded so as to have a volume fraction approaching the critical percolation threshold of the material system and exhibit a conductance that greatly increases with pressure. Sensors may be arranged to form one or more arrays including planar and conformal configurations. The present invention has immediate application in keyboards, intrusion systems, control systems, submarines, ships, sonobuoys, doors, and switches.

7 Claims, 6 Drawing Sheets

HIGH-SENSITIVITY PRESSURE CONDUCTION SENSOR FOR LOCALIZED PRESSURES AND STRESSES

CROSS REFERENCE TO RELATED APPLICATIONS

This application is based upon and claims priority under 35 U.S.C. § 119(e) from U.S. Provisional Patent Application No. 60/512,335 filed Oct. 17, 2003, entitled Pressure Conduction Devices, the contents of which are hereby incorporated by reference.

FEDERALLY SPONSORED RESEARCH AND DEVELOPMENT

None.

BACKGROUND OF THE INVENTION

1. Field of the Invention

The present invention generally relates to a device capable of large conduction changes when locally compressed and decompressed. Specifically, the present invention is a sensor of sufficiently high sensitivity so as to enable pressure and stress measurements.

2. Description of the Related Art

Sensors are critical to the performance of keyboards, intrusion detection systems, and fluid control systems.

Musical keyboards employ carbon contacts to detect the depression of a key and a capacitive strip to measure how hard and fast the key is depressed so as to simulate the dynamic response of an instrument. Keys are susceptible to dirt, moisture, and other contaminants. Mechanical solutions adversely effect pressure detection and penalize the dynamic range of the instrument.

Intrusion systems include optical and laser devices for detection purposes. Devices are difficult to conceal and readily defeatable. Furthermore, such systems are limited in their mapping capability and therefore do not provide a complete record of an intrusion, including, but not limited to, location and time, to resolve direction of travel and speed.

Fluid control systems for cooling, fire suppression, and fuel transport require inline sensors to accurately measure pressure for the active control of valves and pumps. However, such systems must function within a harsh environment including rapidly changing pressures. Diaphragm-based gages offer reliable pressure measurement, even when surrounded by corrosive and high temperature fluids, but are generally too bulky for inline use. Furthermore, low sensitivity and high cost limit the application of diaphragm-based devices to all but the most critical systems.

High-sensitivity pressure sensors are sorely needed for the above referenced applications, as well as for other applications, including submarines, torpedoes, sonobuoys, industrial and commercial keyboards, doors, and switches. Composites having one or more pressure variable properties are critical to a new class of sensors for use within the applications above.

Polymer-metal composites having variable resistance are described in U.S. Pat. No. 4,028,276. Compositions experience an actual change in electric properties, namely, resistance, when compressed by a mechanical load. Practical applications of these materials require a complete and uniform compression of the composite cross its presented area. As such, a large force is required for proper function. Resultantly, polymer-metal composites lack the fidelity necessary to accurately measure pressure and stress and thereby limited to sensing gross magnitudes and differentials.

Pressure conduction composites exhibit a change in conductance in response to a mechanical load. Unlike polymer-metal composites, pressure conduction composites do not experience an actual resistance change. Rather, compression alters the spatial arrangement of conductive particles within a non-conductive matrix as so to enable a change in conduction between particles about the critical percolation threshold of the material system. Small localized mechanical loads or pressures cause a very large change in the "effective" resistance at the output of the composite. This highly localized sensitivity greatly improves the signal-to-noise ratio and usable signal strength from the composite. Furthermore, pressure conduction composites are inherently resistant to the deleterious effects of dirt, moisture, and other contaminants.

Therefore, what is currently required is a high-sensitivity sensor including a pressure conduction composite capable of detecting and measuring pressure and/or stress.

Furthermore, what is currently required is a high-sensitivity sensor including a pressure conduction composite that is sufficiently robust to avoid the deleterious effects of harsh environments.

Furthermore, what is currently required is a high-sensitivity sensor including a pressure conduction composite having a compact, conformal form of minimal volume.

Furthermore, what is currently required is a high-sensitivity sensor including a pressure conduction composite that is easily configurable to enable a matrix arrangement for large spatial applications.

SUMMARY OF INVENTION

An object of the present invention is to provide an electrically and mechanically simple sensor that minimizes signal-processing requirements.

A further object of the present invention is to provide a sensor that is sufficiently robust to avoid the deleterious effects of harsh environments.

A further object of the present invention is to provide a sensor having a compact, conformal form of minimal volume.

A further object of the present invention is to provide a sensor that is easily configurable into a matrix arrangement for large spatial applications.

In its simplest form, the present invention is comprised of a pair of locally resilient conductive layers and a locally resilient pressure conduction composite disposed between and contacting both conductive layers.

In alternate embodiments, the present invention may include at least three locally resilient conductive layers and at least two locally resilient pressure conduction composites, each having a critical percolation threshold. Each composite is disposed between and contacting two locally resilient conductive layers in a multi-layered fashion.

In yet other embodiments, the present invention may include a locally resilient pressure conduction composite, a flexible substrate completely surrounding the composite so as to seal it therein, and a pair of electrical leads contacting the composite and terminating outside of the flexible substrate.

Composites are composed of a plurality of conductive particles electrically isolated within a non-conductive matrix. Conductive particles are loaded at a volume fraction approaching the critical percolation threshold of the material system so as to exhibit a conductance that greatly increases with pressure. Passive and active biasing may be applied via a variety of mechanical, electromechanical, and magnetic devices. Sensors may be arranged to form an array architecture including planar and conformal configurations.

The term "locally resilient" refers to the movement of composite and layers immediately adjacent to a mechanical load. For example, a compression event includes a volumetric reduction of the matrix and localized elastic deformation of the outer layers. A decompression event includes a volumetric expansion of the matrix and localized elastic recovery of the outer layers.

The flexible and pliable composites within the present invention are the functional equivalent of a highly pressure responsive resistor. Since composites may be tailored to a variety of pressure ranges, composites may be color coded to visually identify performance characteristics.

The described invention provides several advantages over the related arts. The invention is inherently more sensitive resulting in more accurate and detailed measurements. The noise component within the usable signal from the present invention is far lower than conventional sensors. The invention is extremely rugged, inexpensive, scalable in size and form, flexible and conformal, and amenable to conductive and non-conductive coatings to improve durability in harsh environments.

BRIEF DESCRIPTION OF THE DRAWINGS

The invention will now be described in more detail, by way of example only, with reference to the accompanying drawings, in which.

REFERENCE NUMERALS

1 Sensor
2 Pressure conduction composite
3 Conductive particle
4 Matrix
5 Conductive layer
6 Conductive layer
7 Force
13 Pressure conduction composite
14 Thickness
15 Perforations
16 Multi-layer sensor
17a–17b Outer conductive layer
18a–18c Inner conductive layer
19a–19d Pressure conduction composite
20 Sensor
21 Outer layer
22 Outer layer
23 Pressure conduction composite
24 Electrical lead
25 Electrical lead
30 Resistor
31 Buffer
32 Communications circuit
34 Interface circuit
35 Microcontroller
36 Wire interface
37 Wireless interface
38 Sensor
39 Rigid structure
40 Force
41 Valve
42 Pipe
43 Pipe wall
44 Electrical leads
45 Communications circuit
46 Sensor
47 Interior surface
48 Exterior surface
49 Sensor
50 Rigid element
26 Electrical contact
27 Electrical contact
28 Seam
29 Sensor
51 Non-conductive layer
52 Non-conductive layer
53 Non-conductive layer
54 Non-conductive layer.

DETAILED DESCRIPTION OF THE INVENTION

Figure 1A:
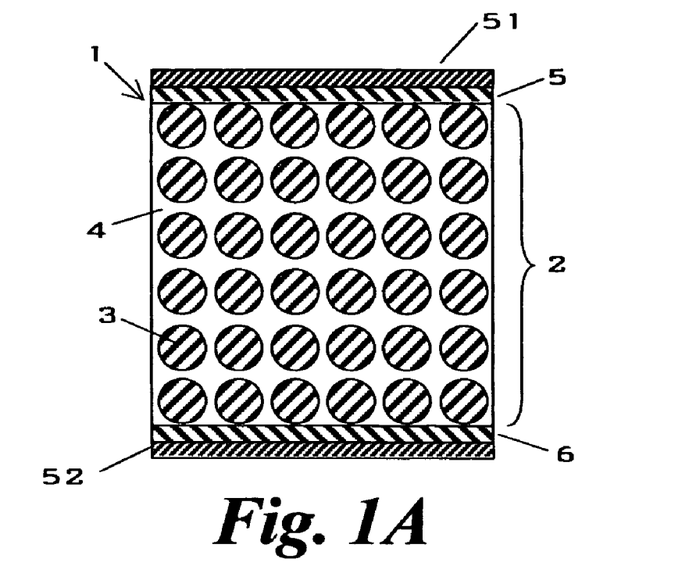
FIG. 1a is a schematic diagram showing a pressure conduction composite, composed of a non-conductive matrix having conductive particles electrically isolated therein, sandwiched between a paired arrangement of conductive and optional non-conductive layers.

Referring now to FIG. 1a, a schematic representation of one embodiment of the sensor 1 is shown having a pressure conduction composite 2 disposed between two conductive layers 5, 6. An optional pair of non-conductive layers 51 and 52 contact the conductive layers 5 and 6, respectively, opposite of the pressure conduction composite 2.

Conductive layers 5, 6 include a variety of materials, such as metals and composites, and a variety of generally planar structures, including plates, foils, films, foams, weaves, and braids. The pressure conduction composite 2 is composed of conductive particles 3 within a non-conductive yet pliable and resilient matrix 4. The matrix 4 is a generally planar solid that surrounds and isolates the conductive particles 3 so as to maximize resistance and minimize conductance thereby preventing current flow between conductive layers 5, 6 at an ambient or biased pressure. Non-conductive layers 51, 52 isolate the sensor 1 so as to prevent electrical current loss from the sensor 1 and to shield the sensor 1 from electrical current external to the device. Non-conductive layers 51, 52 include a variety of non-conducting materials, such as polymers and composites, and a variety of generally planar structures, including plates, foils, films, foams, weaves, and braids. It is preferred for conductive layers 5, 6 and non-conductive layers 51, 52 to be pliable.

Figure 1B:
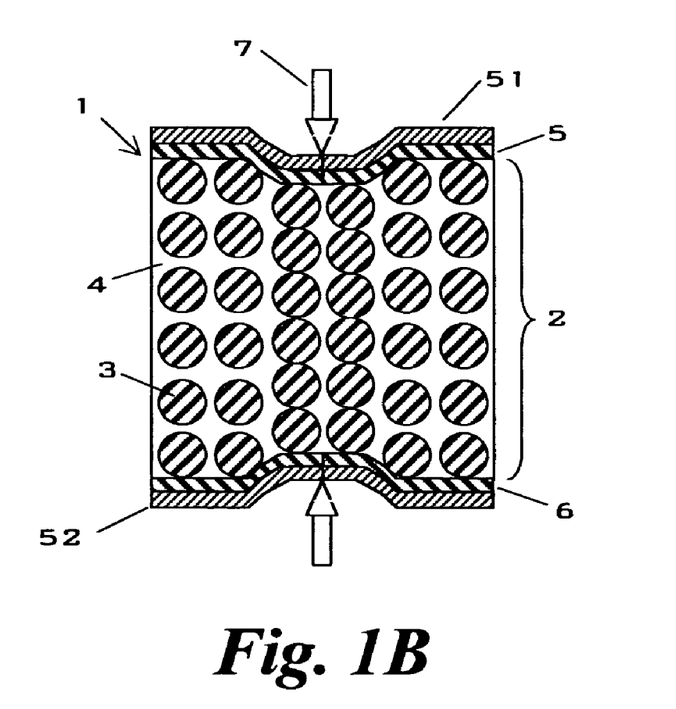
FIG. 1b is a schematic diagram showing sensor from FIG. 1a after localized compression of the composite so as to allow electrical connectivity between particles adjacent thereto.

Referring now to FIG. 1b, the distance between conductive particles 3 decreases with increasing force 7 thereby increasing the effective conductance of the pressure conduction composite 2. In the present invention, force 7 is a mechanical load partially interacting with at least one conductive layer 5, 6 and optionally with at least one non-conductive layer 51, 52, as represented in FIG. 1b. Maximum conductance is achieved when conductive particles 3 and conductive layers 5, 6 are contacting. The matrix 4 should be sufficiently resilient to allow for its recovery after the force 7 is removed. It is preferred for the conductive particles 3 to return to their original or nearly original location within the matrix 4.

The term "locally resilient" refers to the movement of the pressure conduction composite 2, one or more surrounding conductive layers 5, 6, and one or more optional non-conductive layers 51, 52 under and adjacent to a mechanical load. For example, a compression event includes a volumetric reduction of the matrix 4, spatial displacement of conductive particles 3, and localized elastic deformation of conductive layers 5, 6 and nonconductive layers 51, 52. A decompression event includes a volumetric expansion of the matrix 4 to its original or nearly original volume, spatial displacement of conductive particles 3 to their original or nearly original locations, and localized elastic recovery of conductive layers 5, 6 and nonconductive layers 51, 52. Compression and decompression may be assisted by a variety of mechanical, electromechanical, and magnetic devices.

Figure 2:
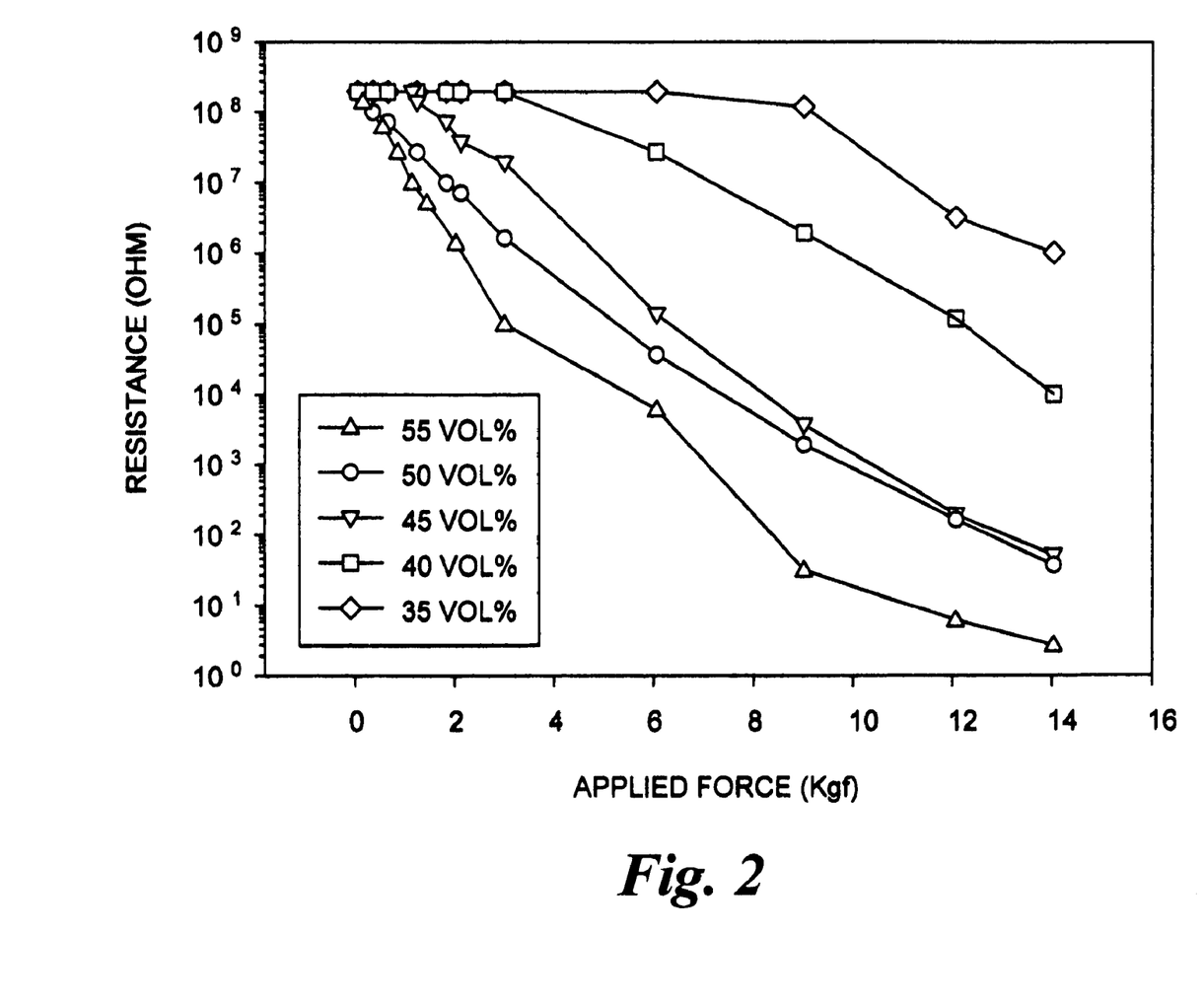
FIG. 2 is a graph showing force dependent resistance for several exemplary titanium-diboride/polymer systems.

Referring now to FIG. 2, resistance-force curves are shown for several exemplary pressure conduction composites 2 having titanium diboride particles within a polymer plate. In general, pressure conduction composites 2 exhibit an extremely large decrease in resistance over a relatively small range of force. The volume fraction of conductive particles 3 influences the resistance-to-force characteristics of the composition thereby allowing the material system to be tailored or tuned for ambient and operating pressures. It is likewise possible for the pressure conduction composite 2 to be actively biased as a function of constant or changing ambient pressure thereby requiring minimal pressure to produce the desired change in conductance.

Referring again to FIG. 1a, stoichiometry, thickness, and feedstock materials greatly influence the resistance-force profile via the properties of sensitivity, signal quality, and pressure range. Stoichiometry relates to the density of particles 3 within the matrix 4. The size and density of particles 3 greatly influence the sensitivity and pressure range. Thickness of the pressure conduction composite 2, conductive layers 5, 6 and non-conductive layers 51, 52 determine the pliability of the sensor 1 and its ability to couple mechanical loads into the material system. In general, it is preferred to have conductive particles 3 at a volume fraction at or near the critical percolation threshold of the material system. Furthermore, it is generally preferred to have the conductive particles 3 randomly dispersed within the matrix 4 so as to avoid a continuous path between conductive layers 5, 6 at initial conditions. Likewise, it is preferred for matrix 4, conductive layers 5, 6 and non-conductive layers 51, 52 to be sufficiently thin so as to insure a low profile, flexible sensor 1 for conformal applications.

The critical percolation threshold is the pressure at and above which the pressure conduction composite 2 exhibits a very large decrease in resistance, which may be as large as six orders of magnitude. Pressures near yet less than the critical percolation threshold ensure the conducting particles 3 to have a spatial separation sufficiently small so as to allow current flow between the conducting layers 5, 6. Pressure conduction composites 2 operating near the critical percolation threshold ensure a sufficiently distinctive change in conduction over a range of pressures so as to allow for the precise measurement of pressure and/or stress.

The matrix 4 may be composed of one or more electrically resistive, compressible and resilient materials including, but not limited to, polymers and elastomers. It is preferred for the matrix 4 to be temperature resistant. Exemplary materials include formulations of polyethylene, polystyrene, polyvinyldifluoride, polyimide, epoxy, polytetrafluoroethylene, silicon rubber, polyvinylchloride, and combinations thereof. Preferred embodiments of the present invention were composed of the elastomer RTV R3145 manufactured by the Dow Corning Company.

Conductive particles 3 may include one or more electrically conductive materials including, but not limited to, metals, metal-based oxides, nitrides, carbides, and borides, and carbon black. It is preferred that conductive particles 3 resist deformation when compressed and have a melt temperature sufficiently above the thermal conditions generated during current flow and interrupt. Exemplary materials include aluminum, gold, silver, nickel, copper, platinum, tungsten, tantalum, iron, molybdenum, hafnium, combinations and alloys thereof, $Sr(Fe,Mo)O3$, $(La,Ca)MnO3$, $Ba(Pb,Bi)O3$, vanadium oxide, antimony doped tin oxide, iron oxide, titanium diboride, titanium carbide, titanium nitride, tungsten carbide, and zirconium diboride.

The pressure conduction composite 2 is fabricated via known methods. For example, the pressure conduction composite 2 may be prepared from high-purity feedstocks, mixed, pressed into a solid, and suffused with oil. Conductive layers 5, 6 are thereafter bonded to the pressure conduction composite 2 via an adhesive or vulcanization process. It was preferred to adhesively bond conductive layers 5, 6 to the pressure conduction composite 2 via an electrically conductive epoxy. Non-conductive layers 51, 52 are likewise bonded to the conductive layers via a thermally resistant adhesive, preferably a pliable epoxy.

Feedstocks include both powders and liquids. Conductive particles 3 were exclusively solid particulates. For example, it was preferred for the feedstock comprising the conductive particles 3 to be a fine, uniform powder, examples including 325-mesh titanium diboride and titanium carbide. The non-conductive matrix 4 was fabricated with either a fine, uniform powder or a liquid with sufficient viscosity to achieve adequate dispersion of conductive particles 3 after mixing. Powder-based formulations were mechanically mixed and compression molded using conventional methods. Polytetrafluorethylene and other polymers may require sintering within an oven to achieve a structurally durable solid. Powder-liquid formulations, examples including titanium diboride or titanium carbide and a silicone-based elastomer, were vulcanized and hardened within a die under low uniaxial loading at room temperature.

In some embodiments, it may be desired to impregnate the pressure conduction composite 2 with a liquid via a method referred to as suffusion. The pressure conduction composite 2 is submerged within a bath of one or more inorganic oils, preferable silicone based, thereby allowing complete infiltration of the liquid into the otherwise solid pressure conduction composite 2. The exposure time of the pressure conduction composite 2 is influenced by the dimensional properties and composition of the solid. For example, a pressure conduction composite 2 having a thickness of 0.125-inch, a width of 0.200-inch, and a length of 0.940-inch and composed of titanium diboride or titanium carbide at a volume fraction of 66 percent and RTV R3145 at a volume fraction of 34 percent was adequately suffused after a 48 hour period.

Conductive layers 5, 6 and non-conductive layers 51, 52 are adhered to the pressure conduction composite 2 either before or after suffusion. If before suffusion, conductive layers 5, 6 and non-conductive layers 51, 52 are placed within a die along with sufficiently mixed composition comprising the pressure conduction composite 2 in the desired sequential order. For example, a matrix 4 composed of a silicone elastomer was adequately bonded to two 0.020-inch thick brass plates and polymer non-conductive layer 51, 52 by curing the otherwise liquid elastomer at room temperature between 3 to 24 hours or at an elevated temperature between 60 to 120 degrees Celsius for 2 to 10 hours. If after suffusion, a silicone adhesive is applied between pressure conduction composite 2 and conductive layers 5, 6 and non-conductive layers 51, 52 and thereafter mechanically pressed until the adhesive is cured.

In some embodiments, it may be advantageous for the pressure conduction composite 2 to be porous. Porosity may be required to tailor the mechanical stiffness, elastic properties and cooling characteristics of the pressure conduction composite 2 without adversely degrading electrical conductance and resistance of the element. Furthermore, porosity may improve the compliance and sensitivity of the sensor 1.

Figure 3:
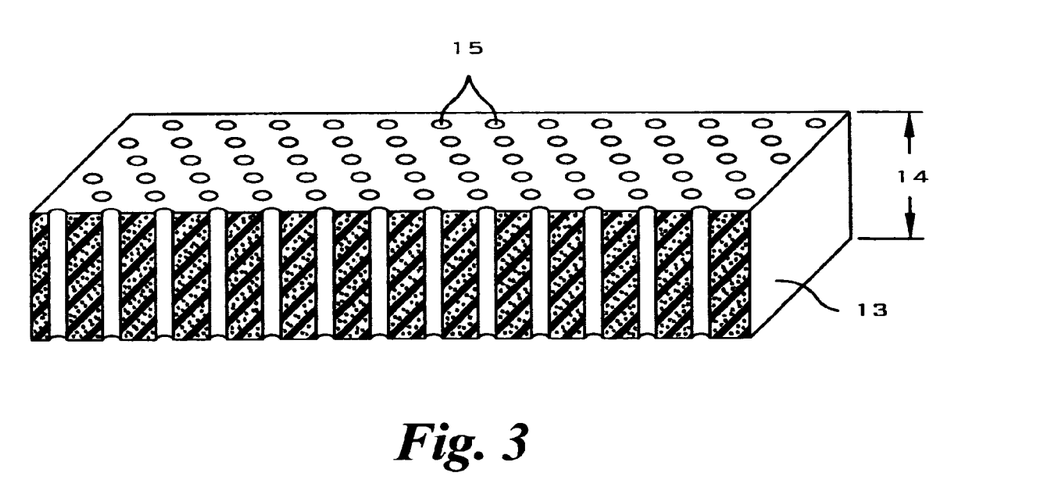
FIG. 3 is a perspective view of a pressure conduction composite with perforations so as to enhance compression and expansion properties of the composite.

Pores may include a variety of shapes including, but not limited to, spheres, ellipsoids, cylinders, and irregular shapes. Referring now to FIG. 3, an exemplary planar disposed pressure compression composite 13 is shown having a plurality of cylindrically shaped perforations 15 traversing the thickness 14 of the element. The dimensions and spatial distribution of the perforations 15 are used to achieve the desired mechanical and electrical characteristics.

Pores may be formed by a variety of manufacturing methods. For example, cavities may be mechanically drilled into the pressure conduction composition 13. Pores may be introduced during mixing of matrix 4 and conductive particles 3 feedstocks via the introduction of gas bubbles. It is likewise possible to include microspheres composed of either a low-density foam or a gas or fluid filled spheres during the mixing process. Also, cavities may be formed during curing of the matrix 4 in an oven whereby localized heating and phase transitions yield void formation and growth.

In yet other embodiments, it may be advantageous to apply a waterproof or heat resistant coating known within the art over sensors 1 described herein to prevent direct contact with the surrounding medium.

A more complex embodiment of the sensor 1 in FIGS. 1a and 1b may include two or more pressure conduction composites 2 bounded by three or more conductive layers 5 or 6 where the outermost conductive layers 5 or 6 each contact an optional non-conductive layer 51 or 52 opposite of the pressure conduction composite 2.

Figure 4:
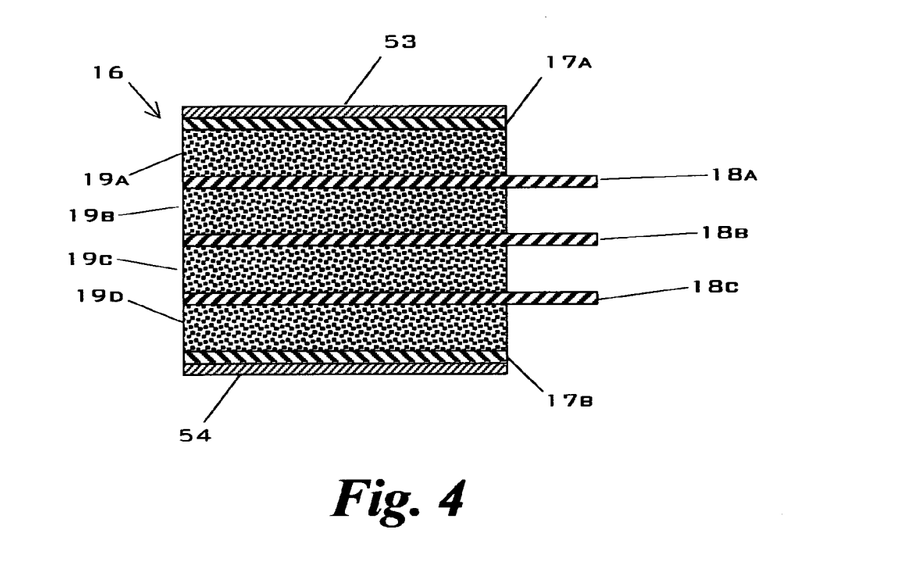
FIG. 4 is a section view of a sensor having a multi-layer arrangement including pressure conduction composite layers bounded by conductive layers with optional non-conductive outer layers.

Referring now to FIG. 4, an exemplary planar disposed embodiment is shown having four pressure conduction composites 19a–19d separated by three inner conductive layers 18a–18c and bounded by a paired arrangement of an outer conductive layer 17a or 17b and a non-conductive layer 53 or 54. Materials and fabrication methods described above are applicable to this embodiment.

Inner conductive layers 18a–18c physically and electrically separate adjacent pressure conduction composites 19a–19d within the multi-layer sensor 16. A voltage is selectively applied to one or more outer conductive layers 17a, 17b and inner conductive layers 18a–18c so as to allow for current flow to one or more outer conductive layers 17a, 17b and/or one or more inner conductive layers 18a–18c. Current flow across one or more pressure conduction composites 19a–19d may be arranged to form a conduction logic circuit facilitating two or more sensitivity ranges for pressure and stress. For example, it may be desired to have two or more pressure conduction composites 19a–19d tuned to one or more separate pressure-conduction or stress-conduction ranges. The multi-layer sensor 16 in FIG. 4 may have a voltage applied to both outer conductive layers 17a and 17b and the center inner conductive layer 18b so as to achieve four conduction pathways. Compression of the pressure conduction composite 19a allows current flow between outer conductive layer 17a and inner conductive layer 18a. Compression of the pressure conduction composite 19b allows currently flow between inner conductive layers 18b and 18a. Compression of the pressure conduction composite 19c allows currently flow between inner conductive layers 18b and 18c. Compression of the pressure conduction composite 19d allows currently flow between outer conductive layer 17b and inner conductive layers 18c. A variety of other conduction logic circuits are apparent from the example above.

Figure 5:
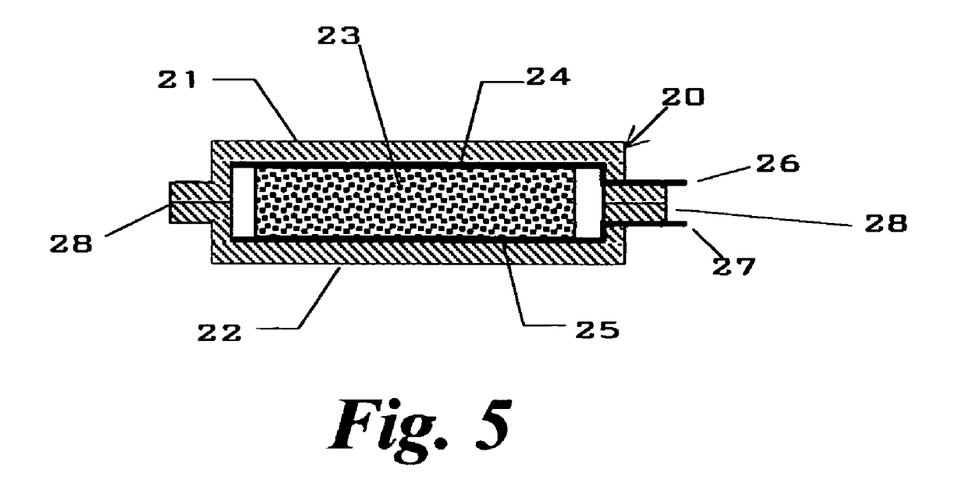
FIG. 5 is a section view of a sensor having a pressure conduction composite hermetically sealed between a pair of flexible substrates with electrical leads thereon.

Referring now to FIG. 5, it may be advantageous in some applications to have the pressure conduction composite 23 sealed from the surrounding environment. In this embodiment, the sensor 20 is shown having a pressure conduction composite 23 disposed between and electrically contacting a pair of electrical leads 24 and 25 and thereafter between a pair of outer layers 21 and 22. Materials and fabrication methods described above are applicable to this embodiment.

It is preferred for the outer layers 21 and 22 to be composed of a flexible, thermally resistant, and non-conducting material, one example being a polyimide. Outer layers 21 and 22 completely cover and surround the pressure conduction composite 23 and electrical leads 24 and 25 so as to prevent their contact with the surrounding environment. Outer layers 21 and 22 are joined via an adhesive or thermally bonded so as to provide a continuous seam 28 about their mutual perimeters. Electrical contacts 26 and 27 are electrically connected to the electrical leads 24 and 25, respectively, and traverse the seam 28 between outer layers 21 and 22 without compromising the seal there between. Electrical contacts 26, 27 facilitate communication of sensor 20 data to acquisition equipment.

In preferred embodiments, the pressure conduction composite 23 was hermetically sealed between a pair of Kapton® thin films, sold by the DuPont Corporation, having copper traces and contact pads along one side thereon so as to form the electrical contacts 26 and 27. Contact pads mechanically and electrically contacted the pressure conduction composite 23 within the sensor 20. Traces and pads were pre-etched onto the Kapton thin film via known flex circuit techniques. Kapton outer layers 21 and 22 were adhered to the pressure conduction composite 23 via a conductive silver epoxy. A pair of pads was provided along the thin film opposite of the pads contacting the pressure conduction composite 23 so as to form the electrical contacts 26 and 27.

Figure 6:
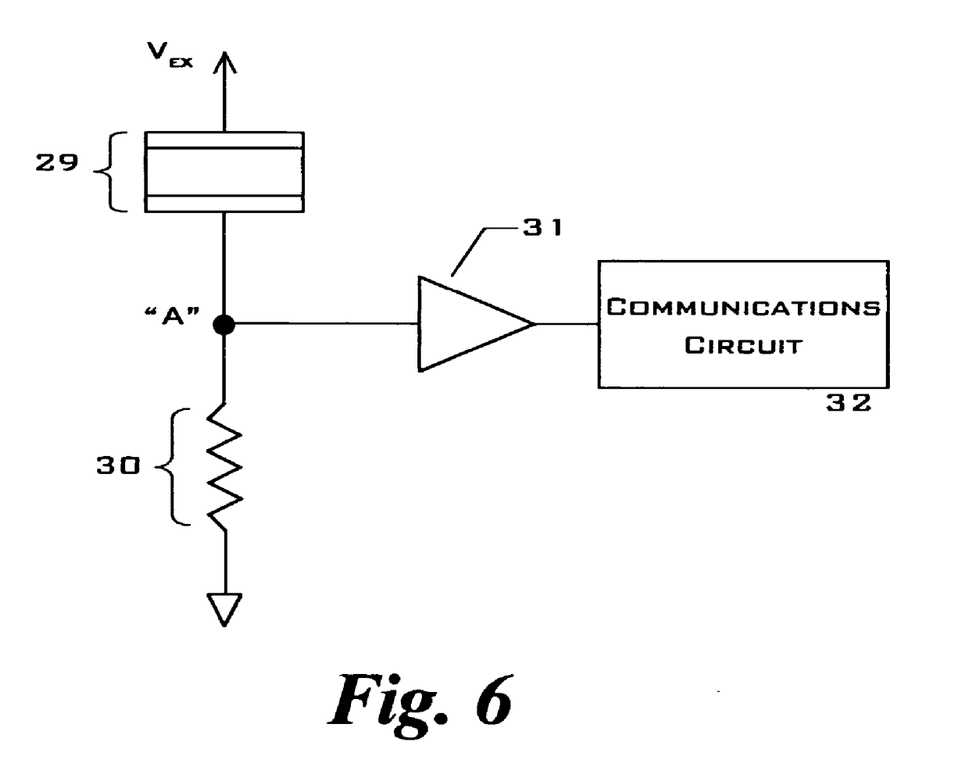
FIG. 6 is an exemplary electrical circuit used to extract and process voltage data from a sensor for the measurement of pressure and stress.

The sensor 1 in FIG. 1a, multi-layer sensor 16 in FIG. 4, and sensor 20 in FIG. 5 each require electrical connectivity to a circuit for the purpose of data retrieval and interpretation. Referring now to FIG. 6, a sensor 29, exemplary of the described devices above, is shown within a divider circuit, although a variety of other circuit designs are possible. The sensor 29 is electrically connected at one end to a resistor 30 in a serial arrangement. The second end of the sensor 29 and resistor 30 are electrically connected to a voltage source of known magnitude, one example being a battery. A buffer 31 is electrically connected at one end between the sensor 29 and resistor 30 at node "A" and at the other end to a communications circuit 32. As described above, the sensor 29 has zero conduction and nearly infinite impedance when no mechanical load is applied across the sensor 29. As such, the voltage at node "A" is zero. The conductance of the sensor 29 increases from zero as a mechanical load of increasing magnitude is applied. The increasing conductance causes the voltage at node "A" to increase accordingly. Thereafter, the voltage at node "A" is amplified and/or filtered by a commercially available buffer 31 and communicated to a communications circuit 32.

The type, density, size, and mass fraction of the conductive particles 3 and matrix 4 within the pressure conduction composite 2 determine the functional relationship between pressure and voltage at node "A". For example, it is possible for the pressure conduction composite 2 to communicate a voltage that is linearly proportional to the mechanically applied pressure within the sensor 29. Likewise, it is possible for the pressure conduction composite 2 to communicate a voltage that is non-linear in relation to the applied pressure. However, it was preferred for the change in conductance to be sufficiently large so as to be distinguishable from electrical noise within the circuit to minimize signal filtering and amplification.

Figure 7:
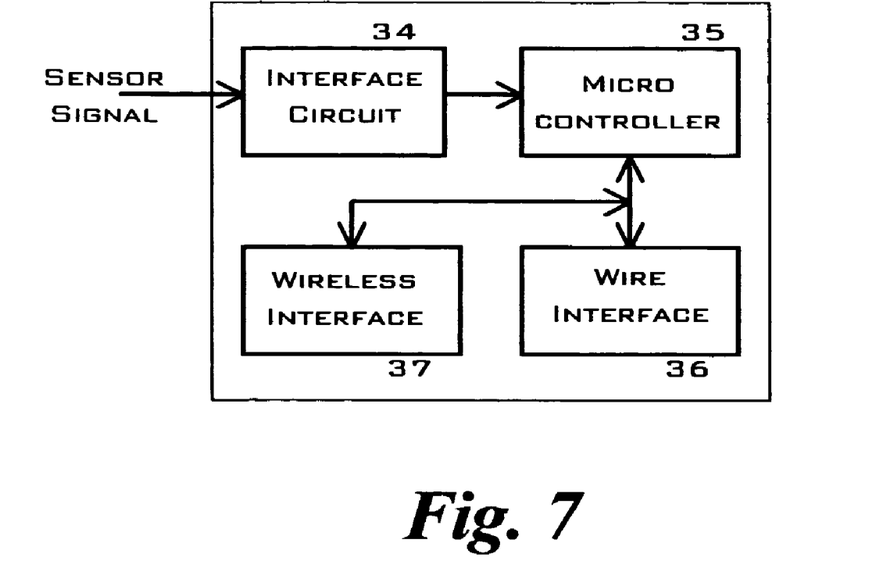
FIG. 7 is an exemplary circuit diagram showing sampling circuit with wire and wireless transmission capabilities.

Referring now to FIG. 7, one possible embodiment of the communications circuit 32 in FIG. 6 is shown including an interface circuit 34 electrically connected to a microcontroller 35, thereafter electrically connected to a wire interface 36 and/or a wireless interface 37. The interface circuit 34 amplifies and/or filters the voltage output from the sensor 29 in FIG. 6 prior to the microcontroller 35. The microcontroller 35 converts the now analog signal to a digital signal, via an analog-to-digital converter (ADC), samples the signal, and organizes the sampled signal data prior to its communication to the wire interface 36 and/or wireless interface 37. The communications circuit 32 may be directly embedded onto or within the sensor 29 or separately disposed so as to provide a smart network of sensors 29 communicating to a master controller. Direct coupling between communications circuit 32 and sensor 29 allows the sensor 29 to also function as a heat sink.

While a variety of commercially available microcontrollers 35 are applicable to the present invention, the MPS430 sold by Texas Instruments, Inc. contains onboard ADCs and communications interface required for remote data uploading to a master controller. The MPS430 supports a variety of asynchronous serial communication protocols compatible with the present invention.

The wire interface 36 may be attached to the MPS430 controller as a flexible Serial Communications Interface (SCI). The SCI allows for both synchronous and asynchronous communication protocols, including RS-232, RS422, RS485, SPI and I2C.

The wireless interface 37 may include, by way of example, a Wi-Port module sold by Lantronix, Inc. capable of communicating data in an asynchronous format over an 802.11b Ethernet network. The Wi-Port also contains internal firmware allowing connection to a variety of TCP/IP protocol stacks including ARP, UDP, TCP, ICMP, Telnet, TFTP, AutoIP, DHCP, HTTP, and SNMP with or without 128 bit WEP encryption for security purposes.

Figure 8:
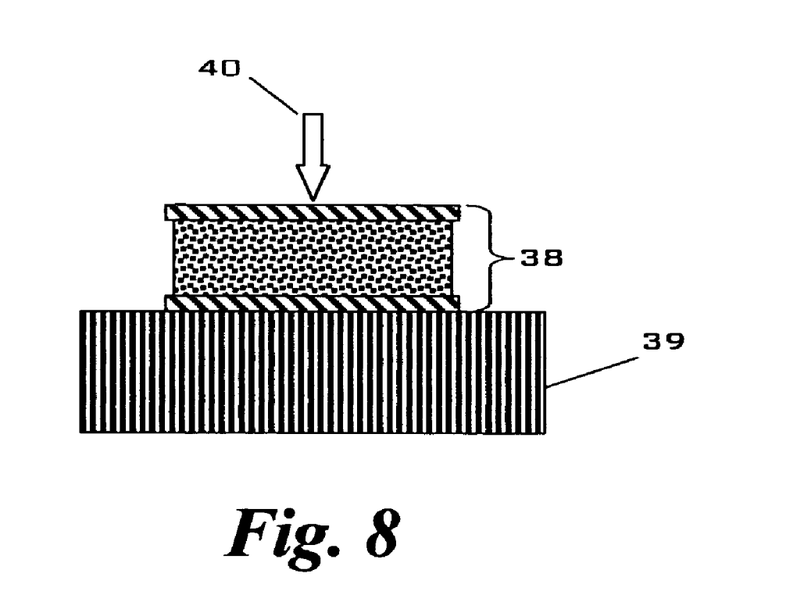
FIG. 8 is a section view of a sensor contacting and attached to a rigid element.

In some applications, it may be advantageous to limit external mechanical loads to one surface along the sensor 38. Referring now to FIG. 8, a sensor 38, exemplary of those described herein, is shown contacting a rigid structure 39 along one surface and having a force 40 applied onto the opposite surface. It is preferred for the sensor 38 to be electrically isolated from the rigid structure 39 via either a non-conductive layer 51, as described above, or a non-conducting epoxy applied between sensor 38 and rigid structure 39. A solid, fluid, or gas impinges the surface opposite of the rigid structure 39 thereby providing either a point or distributed mechanical load.

Figure 9:
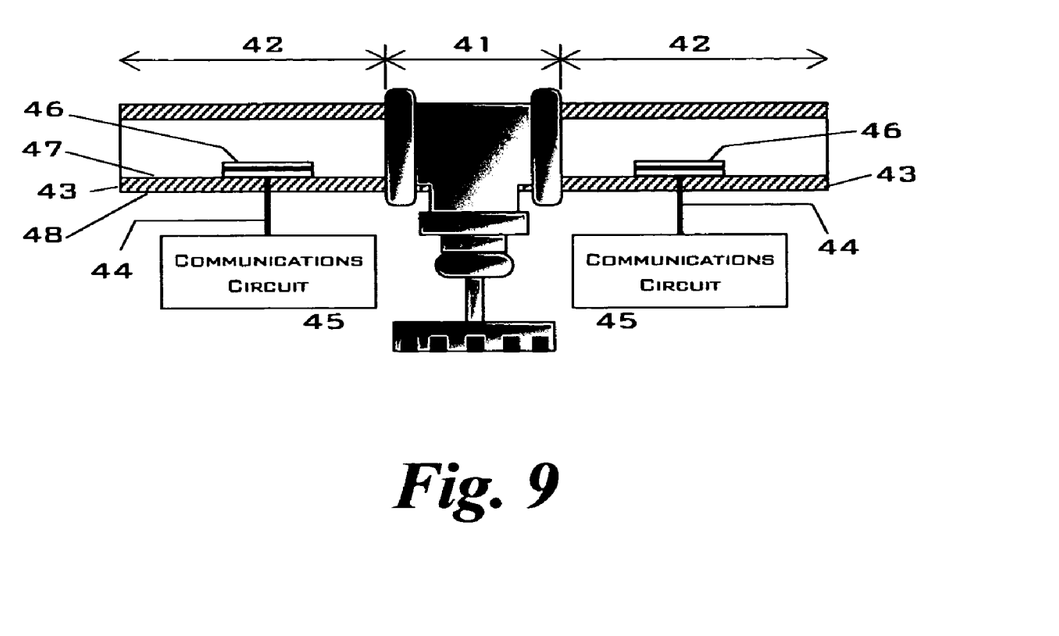
FIG. 9 is a partial section view showing an exemplary application of the present invention within a fluid or gas filled pipe.

Referring now to FIG. 9, a sensor 46, exemplary of the devices described herein, is shown within a pipe 42 at two locations about a valve 41 to demonstrate one specific application of the present invention. The pliable nature of the sensor 46 allows it to conform to the contour of pipe 42. Sensors 46 are bonded via a non-conductive adhesive to the interior surface 47 of the pipe wall 43. A hole is provided through the pipe wall 43 immediately adjacent to the sensor 46 so to allow the sensor 46 to cover and seal the hole and prevent leakage from the pipe 42. Electrical leads 44, similar to those described above, traverse the hole and electrical connects the sensor 46 to a communications circuit 45, as described above. Likewise, the communications circuit 45 may be bonded via a non-conductive adhesive to the exterior surface 48 of the pipe wall 43 to further present leakage from the pipe 42. Two or more sensor 46 may be located within the pipe 42 so as to measure and record pressure, pressure drop, and flow.

Figure 10:
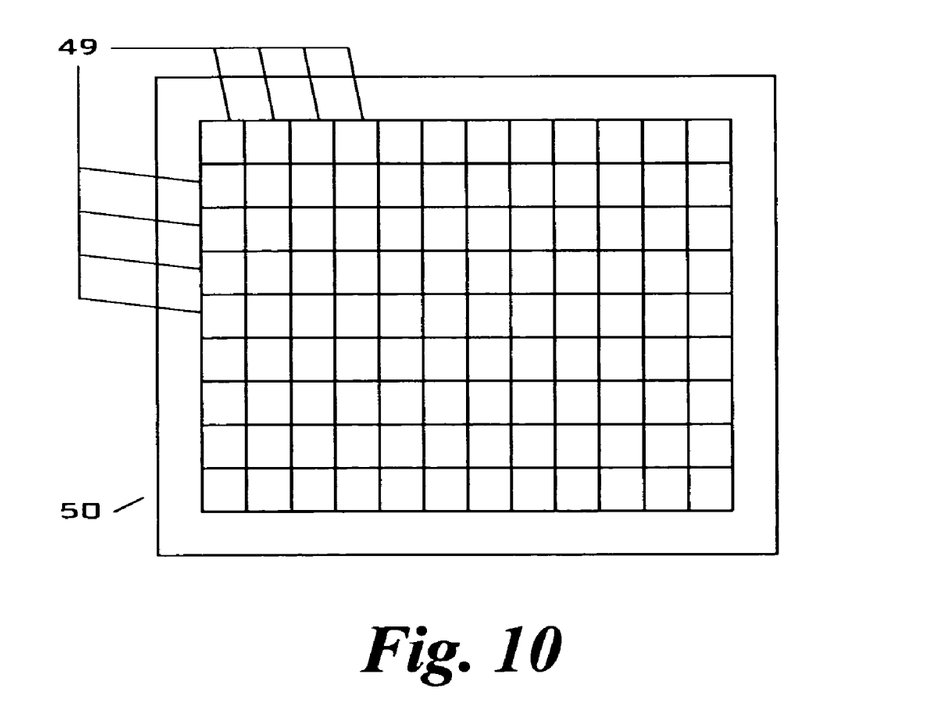
FIG. 10 is a top view showing an exemplary application having a plurality of sensors arranged in an array along a rigid structure.

The low profile and compactness of the present invention lend itself to arrayed configurations. Referring now to FIG. 10, a plurality of sensors 49 may be applied along a planar or non-planar rigid element 50 so as to provide a two-dimensional array. Individual sensors 49 are electrically connected so as to communicate conductance data to a central computer via a row-column architecture similar to that used to control flat panel displays and to control active devices. The latter control architecture is described by the present inventors in co-pending U.S. patent application Ser. No. 10/823,237, entitled Matrix Architecture Switch Controlled Adjustable Performance Electromagnetic Energy Coupling Mechanisms using Digital Controlled Single Source Supply, co-pending U.S. patent application Ser. No. 10/872,974, entitled Thin, Nearly Wireless Adaptive Optical Device, and co-pending U.S. application Ser. No. 10/894, 150, entitled Pressure Sensitive Sensor for Real-Time Reconfigurable Sonar Applications, the contents of which are incorporated by reference.

The rigid element 50 may include a keyboard housing or a floor. In the former application, sensors 49 are applied to the housing so as to provide a plurality of touch sensitive keys or interact with conventional keys. In the latter application, sensors 49 are applied to a floor to form an intrusion detection system. Sensors 49 may be covered by carpet or have an exterior finish representing a specific floor type and style. An intruder activates individual sensors 49 within the floor via the progression of footsteps. Individual signals from the sensors 49 are thereafter communicated via wire or wireless means to a central computer so as to provide location, path and speed data to security personnel.

The description above indicates that a great degree of flexibility is offered in terms of the present invention. Although the present invention has been described in considerable detail with reference to certain preferred versions thereof, other versions are possible. Therefore, the spirit and scope of the appended claims should not be limited to the description of the preferred versions contained herein.

What is claimed is:

1. A high-sensitivity sensor comprising:
   (a) a locally resilient pressure conduction composite having a critical percolation threshold, said locally resilient pressure conduction composite comprising a non-conductive matrix and a plurality of conductive particles near said critical percolation threshold;
   (b) a locally resilient outer layer completely surrounding said locally resilient pressure conduction composite so as to hermetically seal said locally resilient pressure conduction composite therein, said locally resilient outer layer composed of a thermally resistive, nonconductive material; and
   (c) a pair of locally resilient electrical leads oppositely disposed about and contacting an exterior surface along said locally resilient pressure conduction composite within said locally resilient outer layer, said locally resilient electrical leads passing through said locally resilient outer layer so as to hermetically seal said locally resilient electrical leads within said locally resilient outer layer, said locally resilient electrical leads terminating outside of said locally resilient outer layer.

2. The high-sensitivity sensor of claim 1, further comprising:
   (d) a rigid element contacting said locally resilient outer layer opposite of said locally resilient pressure conduction composite.

3. The high-sensitivity sensor of claim 1, further comprising:
   (d) a plurality of perforations through said locally resilient pressure conduction composite.

4. A sensor array comprising a plurality of high-sensitivity sensors of claim 3.

5. The sensor array of claim 4, further comprising a rigid element contacting said locally resilient outer layer of each said high-sensitivity sensor opposite said locally resilient pressure conduction composite.

6. A sensor array comprising a plurality of high-sensitivity sensors of claim 1.

7. The sensor array of claim 6, further comprising a rigid element contacting said locally resilient outer layer of each said high-sensitivity sensor opposite said locally resilient pressure conduction composite.

* * * * *

UNITED STATES PATENT AND TRADEMARK OFFICE
CERTIFICATE OF CORRECTION

PATENT NO.        : 7,080,562 B2
APPLICATION NO.   : 10/966892
DATED             : July 25, 2006
INVENTOR(S)       : Knowles et al.

It is certified that error appears in the above-identified patent and that said Letters Patent is hereby corrected as shown below:

Column 8, Lines 28, 30, and 32
delete "currently"; insert --current--

Column 10
Line 34: delete "electrical"; insert --electrically--
Line 38: delete "present"; insert --prevent--

Signed and Sealed this

Twelfth Day of September, 2006

JON W. DUDAS
*Director of the United States Patent and Trademark Office*